US012788363B2

(12) United States Patent
Carcione et al.

(10) Patent No.: US 12,788,363 B2
(45) Date of Patent: Nov. 10, 2026

(54) USER INTERFACE FOR ULTRASOUND IMAGING SYSTEM

(71) Applicant: BFLY Operations, Burlington, MA (US)

(72) Inventors: Sonya Carcione, Canfield, OH (US); Murad Omar, Miami Beach, FL (US)

(73) Assignee: BFLY Operations, Burlington, MA (US)

( * ) Notice: Subject to any disclaimer, the term of this patent is extended or adjusted under 35 U.S.C. 154(b) by 0 days.

(21) Appl. No.: 18/109,730

(22) Filed: Feb. 14, 2023

(65) Prior Publication Data

US 2023/0255591 A1 Aug. 17, 2023

Related U.S. Application Data

(60) Provisional application No. 63/310,738, filed on Feb. 16, 2022.

(51) Int. Cl.
*A61B 8/00* (2006.01)

(52) U.S. Cl.
CPC .............. *A61B 8/4427* (2013.01); *A61B 8/54* (2013.01); *A61B 2560/0209* (2013.01)

(58) Field of Classification Search
CPC .. A61B 8/4427; A61B 8/54; A61B 2560/0209
See application file for complete search history.

(56) References Cited

U.S. PATENT DOCUMENTS

| | | | | |
|---|---|---|---|---|
| 8,695,429 | B2 | 4/2014 | Urbano et al. | |
| 9,402,601 | B1 | 8/2016 | Berger et al. | |
| 9,667,889 | B2 | 5/2017 | Rothberg et al. | |
| 10,799,913 | B2 | 10/2020 | Bales et al. | |
| 11,179,175 | B2 | 11/2021 | Houser et al. | |
| 2006/0176242 | A1 | 8/2006 | Jaramaz et al. | |
| 2007/0081711 | A1 * | 4/2007 | Kim | G06T 5/50 382/128 |
| 2011/0055447 | A1 | 3/2011 | Costa | |
| 2017/0105701 | A1 | 4/2017 | Pelissier et al. | |
| 2017/0303899 | A1 * | 10/2017 | Willsie | A61B 8/461 |
| 2017/0360397 | A1 | 12/2017 | Rothberg et al. | |
| 2019/0175149 | A1 * | 6/2019 | Dickie | A61B 8/4254 |
| 2020/0129155 | A1 | 4/2020 | Elgena et al. | |
| 2020/0214679 | A1 | 7/2020 | Silberman et al. | |
| 2021/0096243 | A1 | 4/2021 | Gafner et al. | |
| 2021/0186463 | A1 * | 6/2021 | Dickie | A61B 8/0866 |
| 2021/0244386 | A1 | 8/2021 | Bellamkonda et al. | |
| 2021/0330296 | A1 | 10/2021 | Silberman et al. | |
| 2021/0401404 | A1 | 12/2021 | Hagerman et al. | |

* cited by examiner

*Primary Examiner* — Andrew W Begeman

(57) ABSTRACT

User interfaces for medical imaging devices, including devices with hand-held probes used in sterile imaging procedures, and wherein the user interface includes a user-interface button on the hand-held probe and a reconfiguration module operates to reconfigure the button so that the button performs more than one function and can be reconfigured to operate as a control that controls imaging operations and as a control that controls power mode.

18 Claims, 7 Drawing Sheets

USER INTERFACE FOR ULTRASOUND IMAGING SYSTEM

RELATED APPLICATIONS

This application claims the benefit under 35 USC 119 (e) of U.S. Provisional Application 63/310,738, filed Feb. 16, 2022, and entitled User Interface for Ultrasound Imaging System and which is hereby incorporated by reference herein in its entirety.

BACKGROUND OF THE INVENTION

Scientists and engineers have made remarkable advances with medical imaging technologies, including imaging probes that are portable, provide facile use and ready transport and produce clinically excellent images. Such devices allow doctors and other clinicians to use medical imaging for patients who are remote from hospitals and clinics with imaging equipment or who treat patients who are confined to home. As such, these portable systems provide patients access to the excellent care that advanced medical imaging can provide.

Examples of such portable imaging systems include those described in U.S. Pat. No. 10,856,840 which is granted to the assignee hereof. Other systems such as those in U.S. Pat. No. 8,695,429 include imaging devices with wireless data transmission and battery power to reduce the use of cumbersome data and power cables and which conserve battery power by activating a sleep-mode after some period of inactivity.

Although these portable systems work well, medical devices, particularly handheld devices, face a number of operational challenges related to patient care, safety and hygiene and these additional constraints mean there is a remaining need for improved systems.

SUMMARY OF THE INVENTION

A The systems and methods described herein provide, in one aspect, improved User Interface (UI) systems for a portable medical imaging device, providing improved systems that, inter alia, more easily allow a clinician to use a device that will reduce thermal output and conserve power.

In another aspect, the systems and methods described herein provide improved power control features that detect when the operation of an imaging device has suspended and responsive to that suspension, place the device into a low-power mode and reconfigure the UI of the device to configure a sterile control button for releasing the device from its low-power state.

The systems and methods described herein allow a doctor performing a sterile procedure, during which the doctor cannot touch non-sterile surfaces, such as a touch screen, to alter the operation of an imaging probe. This is beneficial because sterile procedures may take a long time. Operational changes to the imaging device during that time, which reduce thermal output or conserve battery power, may improve patient care. In particular, reduction of thermal output can preserve battery life for battery powered units. It can also improve the patient experience and patient comfort.

In one embodiment, the systems include an imaging device having an improved user interface and having a power control module that monitors the use of the system and enters the system into a low-power mode if use has been suspended for a predetermined and set period of time and, once in the low-power mode, the system activates a reconfiguration module to reconfigure a UI button. The reconfiguration module reconfigures a UI control button on the probe of the imaging device to operate as a wake-up button control that, when activated, removes the imaging device from the low-power mode and places it into an operational power mode suitable for imaging operations.

In one embodiment, the systems and methods described herein provide a medical imaging device having at least one UI button that connects to a reconfiguration module. The reconfiguration module monitors the UI button and determines if the button is activated. The reconfiguration module responds to the operating power state of the imaging device to detect whether the device is operating in a low-power mode or in a power mode suitable for imaging operations. The reconfiguration circuit multiplexes an activation signal from the UI button based, at least in part, on the power mode of the imaging device. To this end, the reconfiguration module responds based at least in part on whether the device is in an imaging power mode. If the device is in an imaging power mode, the reconfiguration module can generate an image capture signal that it may pass to the CPU to instruct the CPU to capture an image, or activate various functions such as, but not limited to, making battery status readings, performing imaging control such as for controlling depth, controlling gain, switching modes, turning color on and/or off, controlling a wireless pairing process, or for soft resetting of the probe. Alternatively, if the imaging device is in a low-power mode the reconfiguration module may deliver a signal to a power control module. The power control module may initiate a wake-up process that releases the imaging device from the low-power mode and places the imaging device in an imaging power mode so that the device is ready for imaging operations.

As such, the clinician may use the UI button as a UI that controls both imaging operations and power control. The improved UIs described herein are understood to reduce the need to have the clinician monitor the power state of the device during use. They further reduce the need to have control buttons for both image capture and power-up control. They still further reduce the need for the clinician to use control buttons located on components of the imaging device that may lack sterility.

In certain embodiments the imaging devices described herein may include a probe and a handheld device. The UI button may be positioned on the probe or the handheld device. In one embodiment, the UI button, whether on the probe or the handheld device, may be a physical button of the type operated by applying a mechanical force to the button. In other optional embodiments the UI button may be a software control of the type presented on a touchscreen display. Further optionally, the reconfiguration module may be part of the probe or the handheld device. In operation, releasing the imaging device from a low-power mode and to a power mode ready for imaging may include releasing the probe from a low-power mode, releasing the handheld device from a low-power mode or releasing both the probe and the handheld device from a low-power mode.

In certain embodiments the imaging device has multiple UI buttons and may have one or more UI buttons on the probe and one or more UI buttons on the handheld device. When in a low-power mode, one or more of the UI buttons may be configured to release the imaging device from low-power mode. Once the imaging device is released from the low-power mode, the UI buttons may be configured to activate various functions such as, but not limited to, making battery status readings, performing imaging control such as for controlling depth, gain, capturing one image or a series of images, switch modes, color on and/or off, controlling a wireless pairing process, and for soft resetting of the probe.

In optional embodiments, the device has a data memory, which may be positioned in the probe or in the handheld device, that stores a preset parameter. The preset parameter represents a preset operation. A preset operation provides one or more parameter settings for a particular type of imaging operation, such as for imaging a patient's carotid artery. In one embodiment, the reconfiguration module determines if the device is in a low-power mode and determines if the stored preset parameter represents a procedure for which the clinician will want sterile conditions. If the device is in a low-power mode and if the preset parameter is for an operation indicated for sterile conditions, in one embodiment the reconfiguration module may generate a signal for the power control circuit to initiate a wake-up mode that releases the device from low-power mode.

In other embodiments, the systems described herein include an ultrasound imaging system having a handheld device and a probe that generates ultrasound images and comprising a UI control button disposed on the probe, a power control module configured to activate a low-power mode to reduce power consumed by at least one of the handheld device and the probe, and to generate a wake-up configuration signal representative of a command to reconfigure a function of the UI control button, and a reconfiguration module configured to receive the wake-up configuration signal and reconfigure an interface coupled to the UI control button to detect activation of the UI control button and, in response to activation of the UI control button, to deactivate the low-power mode and have the handheld device and the probe consume power sufficient to perform imaging procedures.

In further embodiments, the ultrasound imaging system may further comprise a timer module configured to generate a timeout signal, wherein the power control module activates the low-power mode responsive to receiving the timeout signal from the timer module wherein the timeout signal represents expiration of a timeout period. Additionally, the system may comprise a data memory that stores a preset timeout parameter representative of a timeout period, and wherein the timer module counts down in response to the stored preset timeout period to generate the timeout signal. Further optionally, the system may comprise a preset memory for storing preset parameters for configuring the probe for a predetermined imaging procedure and wherein the power control module is configured to process the preset parameters to determine whether the preset parameters indicate that the predetermined imaging procedure is a sterile imaging procedure and to activate a low power mode if the preset parameter indicates a sterile imaging procedure. Optionally, the preset memory may store preset parameters for a plurality of predetermined imaging procedures and stores a timeout period for each of the respective predetermined imaging procedures. Further, the preset memory may store an override parameter representative of an operator instruction for the reconfiguration module to override the preset parameters for a predetermined imaging procedure and implement the operator instruction for reconfiguring the UI control button. Further, the reconfiguration module may deactivate the low-power mode by sending a signal to the power control module to activate a power mode sufficient to perform imaging procedures.

In further embodiments, the ultrasound imaging system may include an image comparator module to detect changes in a sequence of ultrasound images and to reset the timer module responsive to detecting changes in the sequence of ultrasound images.

In certain embodiments, the ultrasound imaging system has a probe that is a hand-held ultrasound probe having a transducer for transmitting and receiving ultrasound signals and a housing connected to the transducer and shaped to allow a clinician to grip the probe with a hand and thereby position the transducer proximate a patient and wherein the UI control button is disposed on the housing at a location that can be reached by a hand holding the probe. In some embodiments the UI control button, when not in low-power mode, may operate the probe to generate a reading of remaining battery power or perform an image capture procedure to capture ultrasound images.

In another aspect, methods are disclosed for ultrasound imaging using a handheld device and a probe with a UI control button disposed on the probe, and including activating a low-power mode to reduce power consumed by at least one of the handheld device and the probe, generating a wake-up configuration signal representative of a command to reconfigure a function of the UI control button, and in response to the wake-up configuration signal, reconfiguring an interface coupled to the UI control button to respond to activation of the UI control button by deactivating the low-power mode and having the probe or the handheld device enter a power mode that consumes an amount of power sufficient to perform ultrasound imaging procedures. The method may further include providing a timer module configured to generate a timeout signal, and activating the low-power mode responsive to the timeout signal from the timer module wherein the timeout signal represents expiration of a timeout period. The method may further include storing a preset timeout parameter representative of a timeout period, and wherein the timer module counts down from the stored preset timeout parameter to generate the timeout signal. Further embodiments may include storing preset parameters for configuring the probe for a predetermined imaging procedure and reconfiguring the interface if the preset parameters indicate a sterile imaging procedure and refrain from reconfiguring the interface if the preset parameters indicate a non-sterile imaging procedure. Storing preset parameters may include storing preset parameters for a plurality of predetermined imaging procedures and storing a timeout period for each of the respective predetermined imaging procedures. Optionally, the method may include providing a memory for storing an override parameter representative of an operator instruction to override the wake-up configuration signal and thereby prevent reconfiguring the interface.

In further embodiments, the method may include detecting changes in a sequence of ultrasound images and resetting the timer module to the timeout period in response to detecting changes in the sequence of ultrasound images. Optionally, detecting changes in a sequence of images may include performing an edge detection and comparison process to determine whether similar edges of images the sequence of images are changing.

In further embodiments, the method may provide the probe as a hand-held ultrasound probe having a transducer for transmitting and receiving ultrasound signals and a housing shaped to allow a clinician to grip the probe with a hand and disposing the UI control button on the probe at a location that can be reached by a hand holding the probe. Optionally the UI control button, when not in low-power mode, may operate the probe to generate a reading of remaining battery power or perform an image capture procedure to capture ultrasound images.

BRIEF DESCRIPTION OF DRAWINGS

The systems and methods described herein are set forth in the appended claims. However, for purpose of explanation, several embodiments are set forth in the following figures.

DETAILED DESCRIPTION

In the following description, numerous details are set forth for purpose of explanation. However, one of ordinary skill in the art will realize that the embodiments described herein may be practiced without the use of these specific details. Further, for clarity, well-known structures and devices are shown in block diagram form to not obscure the description with unnecessary detail.

Figure 1:
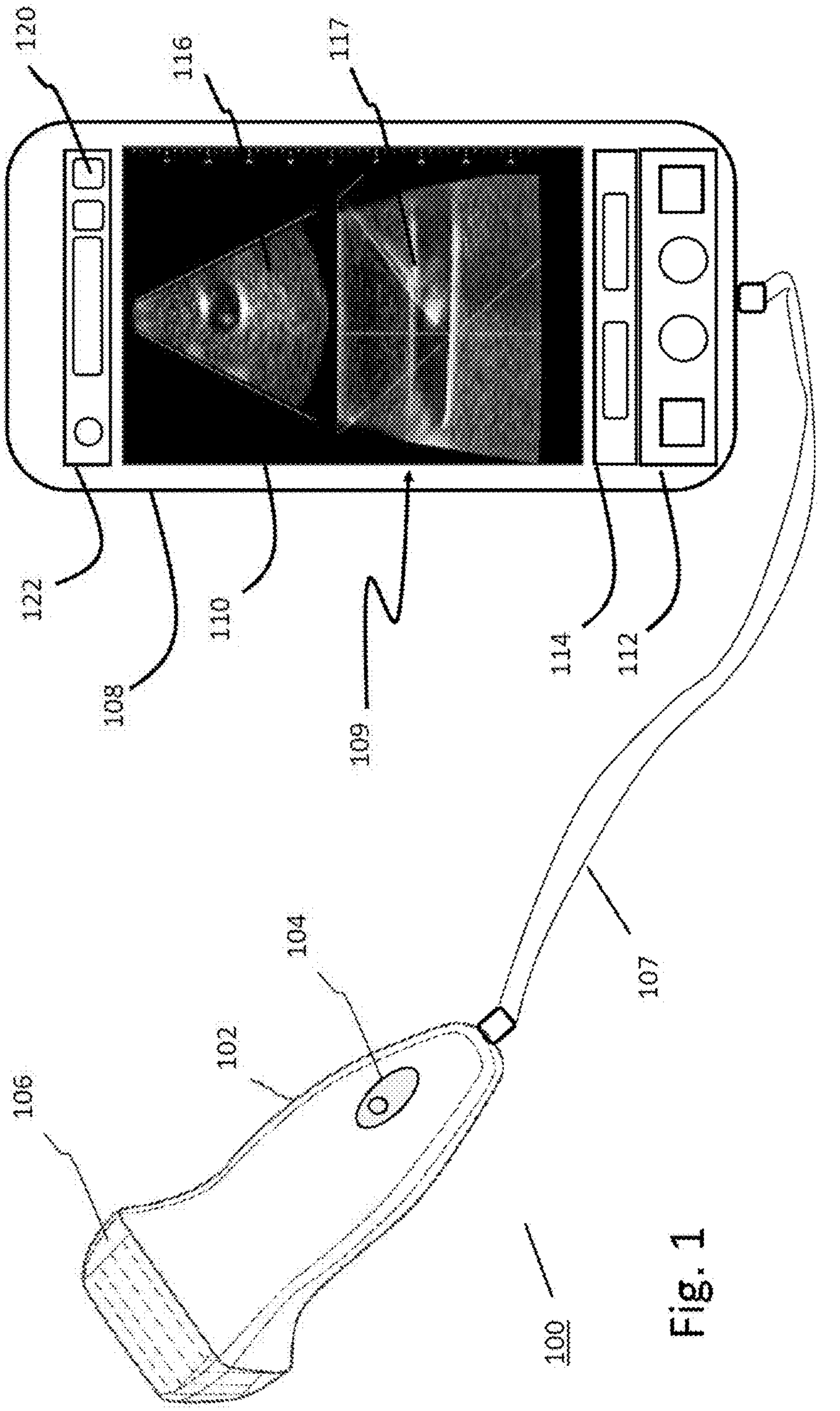
FIG. 1 depicts one embodiment of the systems described herein.

In one embodiment, the systems and methods described herein include, among other things, the system 100 depicted in FIG. 1. FIG. 1 depicts that system 100 includes a probe 102 and a handheld device 108. The probe 102 has a UI control button 104 and a transducer head 106. The probe 102 is coupled by a cable 107 to a handheld device 108, depicted in FIG. 1 as a mobile phone. The depicted handheld device 108 is executing an application 109 that collects data, including image data, from the probe 102. The application 109 may display an image within the image window 110 and may display within software UI windows, such as the software UI window 112, one or more controls for operating the probe 102.

The probe 102, in this embodiment, is an ultrasound probe of the type disclosed in U.S. Pat. No. 10,856,840, assigned to the assignee hereof. The probe 102 is a handheld ultrasonic imaging probe that can be used by the clinician to image a patient and collect medical images useful in the clinical process of diagnosing and treating the patient. In the depicted embodiment the probe 102 is a handheld battery powered unit, although in other embodiments the probe 102 may draw power from the handheld device 108 or from a remote power supply. The probe 102 has a transducer head 106 that the clinician may place against the tissue of the patient, such as by placing the transducer head 106 in contact with the patient's chest proximate to the heart of the patient or proximate the carotid artery. The depicted probe 102 has a single UI control button 104, although in other embodiments there may be more than one UI control button. In typical operation, the clinician uses the UI control button 104 as a UI by which the clinician may get a reading of remaining battery power or in other embodiments the UI control button 104 may activate various other functions such as image capture operations that cause the application 109 executing on the handheld device 108 to store one of the images generated by the transducer head 106. That application 109 may render the captured image in the image window 110 for the clinician to view. The UI window 112 may provide the clinician with a series of optional user interface controls that the clinician may use to operate the application 109 executing on the handheld device 108 to change how the captured image is rendered, store the image, mark the image, and perform other types of operations useful during the tomographic procedure.

During a tomographic procedure, the clinician adjusts the position and angle of the probe 102 until an image of interest appears in the image window 110. In some embodiments, the clinician may activate the UI control button 104 to capture images to study, or activate various functions such as, but not limited to, making battery status readings, performing imaging control such as for controlling depth, controlling gain, switching modes, turning color on and/or off, controlling a wireless pairing process, or for soft resetting of the probe. The depicted UI control button 104 is a mechanical button and activation of the UI control button 104 is, in this embodiment, done through the conventional means of applying a mechanical force, typically force from the clinician's thumb against the UI control button 104. The UI control button 104 will detect the applied mechanical force of the clinician and generate an electrical signal that can be processed by probe 102.

In the embodiment depicted in FIG. 1, the handheld device 108 is a programmable device that runs the application 109 that, for example, performs the image display functions, user interface functions, such as allowing the clinician to select presets and capture images from the image stream, and configures the system 100 with any selected preset parameters. In this embodiment, the handheld device 108 may be a smart phone, a tablet, or any other suitable handheld device capable of running application programs and of supporting a data connection to the probe 102. In the depicted embodiment the handheld device 108 couples to the probe 102 by way of the cable 107. However, in alternative embodiments, the handheld device 108 and the probe 102 may have a wireless connection of the type suitable for transferring data and control signals between the two devices. In one example, the wireless connection may be the Bluetooth protocol (IEEE 802.15.1), ultra-wideband (UWB, over IEEE 802.15.3), ZigBee (over IEEE 802.15.4), or Wi-Fi (over IEEE 802.11) connection or a connection using some other protocol for short-range wireless communications, preferably with low power consumption. However, any suitable wireless technology may be used including those that work with narrow bands, employ optical communication, or which use some other suitable technique for exchanging information between the probe 102 and the handheld device 108.

In the embodiment depicted in FIG. 1 the transducer head 106 includes an array of ultrasonic transducer elements. The array of ultrasonic transducers may be an array of MEMs transducer devices, such as an array of capacitive micromachined ultrasonic transducers (CMUTs) or an array of piezoelectric micromechanical ultrasonic transducers (PMUTs), that are capable of generating ultrasonic waves, including beamformed ultrasonic waves and detecting ultrasonic waves as they return from the patient. In one embodiment, the depicted transducer head 106 includes thousands of transducer elements that operate in coordinated action to create the ultrasound beam used for the image collection. In one example, the transducer head 106 includes a two-dimensional array of thousands of transducer elements formed on a semiconductor die or chip. The die or chip may, in certain embodiments, further contain on-chip processing circuitry including more than one thousand analog-to-digital converters and amplifiers. Embodiments of transducers formed on a semiconductor die or chip are shown in more detail in U.S. Pat. No. 9,067,779 and in US application US2019/0275561. Embodiments of on-chip processing circuitry are shown in more detail in U.S. Pat. No. 9,521,991. In other embodiments, the transducer head may use PMUTs and the A/D converters and amplifiers may be on separate chips or dies and the chips and dies may be mounted on a circuit board or boards. In operation, the transducer head 106 detects ultrasonic waves returning from the patient and these waves may be processed by processing circuitry formed on the same chip as the transducers, a signal processor, a CPU, an FPGA, or any suitable type of processing device, or any combination thereof, which may process the returned ultrasound waves to construct image data. That image data may be used by the application 109 running on the handheld device 108 to create images for the clinician.

In the depicted embodiment, the executing application 109 may display the constructed images, including video images, such as the ultrasound images 116 and 117, on the image window 110 so that the clinician can see live images of the patient as those images are being generated by the probe 102. In the depicted embodiment, the application 109 also provides a UI window 112 that has a series of software control buttons, sometime called widgets, that the clinician may use for controlling the operation of the probe 102. These controls allow the clinician to change how images, such as image 116 and image 117, are rendered, captured, and displayed on the handheld device 108. In the embodiment of FIG. 1, the application 109 further has a menu 114 that depicts a preset selected by the clinician and an indication of the view selected for the clinician. In the depicted example the application 109 renders and displays in the video images 116 and 117 taken during a vascular access procedure. In this example, the system 100 is configured with a needle visualization preset. For clarity it is noted that this needle visualization preset may be employed by the system 100 regardless of whether the system 100 is also employing the auto-freeze feature described herein. This needle visualization preset configures the system 100 with operating parameters selected for capturing clinically useful images of a procedure that involves a hypodermic needle entering the vasculature of the patient. In this example preset, the handheld device 108 overlays a B-mode ultrasound image, generated using parameters set for visualizing an inserted needle, on top of a B-mode image obtained with parameters set for normal vascular imaging. The menu 114 may include text boxes that display text representing the preset used during the ultrasound imaging and that the images are displayed with a biplane view. Biplane views may be understood as displays of two planes of imaging, one along the longitudinal axis of the probe and the other along the transverse axis of the probe. In the depicted example, the longitudinal axis view is displayed on the bottom of the screen and the transverse axis view is displayed on the top of the screen, to provide a perpendicular plane of view of the patient lumen.

In any case, FIG. 1 illustrates that the system 100 allows the clinician to carry out an ultrasound imaging study of a patient. The study may involve a vascular access, cardiac valve function, pre-natal observations, lung capacity or any other study that will benefit from ultrasound imaging. The clinician can select a preset suited for the study and the preset will have parameters, such as depth of penetration and frame rate, that the imaging device system will use to carry out the imaging.

While generating images for the clinician, the transducer head 106 may generate heat due to the circuitry in the transducer head 106, such as the A/D converters and amplifiers. Consequently, in the embodiments described herein, the probe 102 has a low-power mode that reduces the consumption of power by circuitry (e.g., circuitry formed on the same chip as the transducers) within transducer head 106 as well as other components of the probe 102, such as any CPU, signal processing unit, FPGA and other such circuits within the probe 102.

In one embodiment, the low-power mode is activated by an auto-freeze function in which the system 100 automatically puts the probe 102 and/or the handheld device 108 into a battery conservation mode after device inactivity has been detected. The auto-freeze feature may include a timer maintained by the system 100. In one embodiment, the timer tracks the amount of time between events, where the events are indications that the probe 102 is in use by the clinician. Such events may include a sequence of changing images generated by the probe 102 and thereby indicating that the clinician is using the probe to collect images of the patient. In other embodiments, the system may detect events by monitoring inputs such as the activation of the UI control button 104, or inputs received through the UI window 112, or in those embodiments having accelerometers, gyroscopes, magnetometers or other motion sensors, movement of the probe 102. If the duration of time from the last event exceeds a set threshold timeout period, for example ninety seconds, the system 100 may automatically place the transducer head 106 and select other components of the system 100 into a low-power mode.

In low-power mode typically little to no power is consumed by the transducer head 106. Similarly, in low-power mode a signal may be sent to one or more of the on-board CPUs, FPGAs, and/or signal processors to activate functionality to reduce power consumption by those elements. In some embodiments, the CPUs, FPGAs, and/or signal processors that are designed into the probe 102 and handheld device 108 are of the type that have a built-in low-power mode function. In such embodiments, an activation signal applied to the CPUs, FPGAs, and/or signal processors may activate that low-power mode function to place CPUs, FPGAs, and/or signal processors into a low-power mode. In any case, these particular embodiments have an auto-freeze feature that will place the system 100 into a low-power or "sleep" mode when the system 100 detects that use of the system 100 has been suspended as indicated by lack of use of the system for longer than a predetermined and set timeout period.

In one embodiment, the application 109 implements an auto-freeze function by comparing successive images within a stream of images generated by the probe 102 to detect changes within the image stream. The application 109 also monitors a timeout period and if the application 109 fails to detect changes within the image stream before expiration of the timeout period, the application 109 may place the system 100 into a low-power mode. In one embodiment, placing the system 100 in low-power mode essentially freezes the probe 102 and prevents the probe 102 from generating a stream of ultrasound images.

In one embodiment, the timeout period may be implemented by having the application 109 store a data value in a data memory where the data value represents a timeout period, such as a specific number of seconds. In one example, an integer value between 0 and 255 may be stored in a data memory and the value may represent a number of seconds. The application 109 may include a timer function and the timer function will use a clock on the handheld device 108 to count down the number of seconds that correspond to the stored integer value. For example, a stored integer value of 90 will instruct the timer function to count down 90 seconds. Preset parameters may include a timeout period value, such as a value between 0 and 255, and that value will be loaded into the data memory for use by the timer function as part of the preset configuration. If successive-in-time images lack sufficient variation during the timeout period, for example ninety (90) seconds, for a procedure such as a vascular access preset, or twenty (20) seconds for conventional B-mode scanning procedure, then the application 109 places the system 100 into a low-power mode.

The application 109 may monitor the UI control button 104 on the probe 102 to detect when the UI control button 104 is pressed and activated. Responsive to detecting the UI control button 104 being activated, the application 109 will, if in a low-power mode, transition the system 100 from the low-power mode to a power mode for imaging. This essentially "unfreezes" the probe 102 and allows the probe 102 to generate a stream of ultrasound images that can be transmitted to the handheld device 108 for display to the clinician.

In FIG. 1 the application 109 may operate the handheld device 108 to display an icon 120 within menu 122. The icon 120 may present a color, such as yellow or green, that indicates to the clinician the power mode of the system 100 wherein yellow may be for low power and green for a power mode suitable for imaging. Optionally, the icon 120 may present a third color, such as orange, to indicate that the system 100 is in a transition period between two power modes, such as a transition between a low-power mode and a power mode suitable for imaging operations. The color of the icon, in this example whether yellow or green, will also indicate to the clinician the function configuration of the UI control button 104. In this example, the icon color may be yellow to indicate that the UI control button 104 is configured to control transition from a low-power mode to a power mode suitable for imaging or may be green to indicate the UI control button 104 is configured for image capture or another function such as, but not limited to, making battery status readings, performing imaging control such as for controlling depth, controlling gain, switching modes, turning color on and/or off, controlling a wireless pairing process, or for soft resetting of the probe.

In certain embodiments of the systems and methods described herein one of the preset parameters may be a timeout period representative of a period of time during which the system 100 monitors the image stream to detect changes in the images. If after the timeout period expires, the system 100 determines that the image stream lacks variation between successive images, the system 100 may enter a low-power mode. In certain other embodiments of the systems and methods described herein the timeout period is a parameter that is independent of preset and constant for all procedures. In still other embodiments, the timeout period may be a parameter that controls for imaging procedures that were not associated with a preset by the clinician but may be overridden if a preset is selected that has an associated timeout period.

Figure 2:
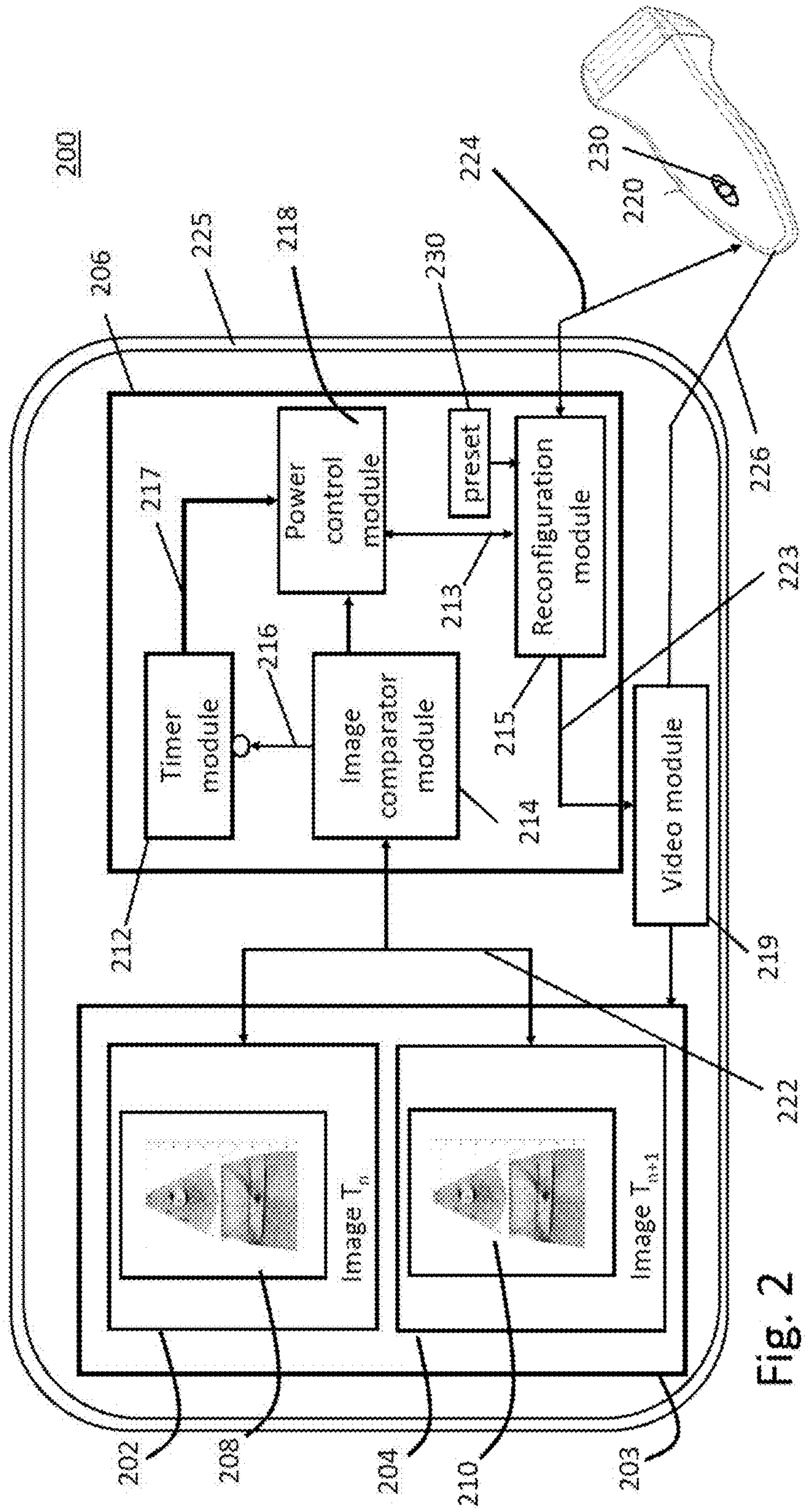
FIG. 2 depicts pictorially an application executing on the handheld device of FIG. 1 for controlling transitions between the power modes.

FIG. 2 depicts pictorially and in more detail a system 200 that has a handheld device 225 executing an application 206 that may reconfigure the operation of the UI control button 230 on the probe 220 to allow the control button 230 to release the system 200 from low-power mode. The application 206 may be a computer program executing on a processor built within the circuit board of the handheld device 225. For clarity and ease of illustration, the application 206 is depicted as a functional block diagram. The functional blocks of application 206 include a timer module 212, an image comparator module 214, a power control module 218 and a reconfiguration module 215. The handheld device 225 also includes a video module 219 for handling video tasks, such as capturing streams of video data generated by the probe 220 and rendering the video on the display of the handheld device 225. In one embodiment the video module 219 is an application that executes on the handheld device 225 and executes as a separate application from the application 206. Those of skill in the art will recognize that each of the depicted functional blocks can be implemented as computer code instructions for performing the functions indicated by the respective functional block. The development of such applications that execute on a handheld device such as a smartphone or tablet and that carry out the depicted functions of the application 206 is well known to those of skill in the art. Techniques for developing such applications are set out in for example, Alebicto et al., Mastering iOS 14 Programming: Build professional-grade iOS 14 applications with Swift 5.3 and Xcode 12.4, 4th Four ed.; Packt Publishing Ltd (2021).

FIG. 2 further depicts that the handheld device 225 communicates with the probe 220 via two data paths, data path 224 and data path 226. Data path 224 carries a control signal from the UI control button 230 to the reconfiguration module 215 of the application 206. Through data path 224, the reconfiguration module 215 may detect when the UI control button 230 has been activated. Data path 226 carries a stream of ultrasound data to the video module 219. The stream of ultrasound data may comprise a time sequence of ultrasound images generated by the probe 220. The video module 219 delivers those images into the data memory 203 and carries out the video processing functions needed to have the images prepared for rendering on the display of the handheld device 225.

FIG. 2 further depicts that the data memory 203 of the handheld device 225 has two memory spaces 202 and 204. The image comparator module 214 employs these memory spaces 202 and 204 to store two ultrasound images 208 and 210. The image comparator module 214 obtains these images 208 and 210 from the stream of image data that was delivered into the data memory 203 by the video module 219. In the example pictured, the images 208 and 210 are sequential in time and the memory space 202 stores image 208 marked with time mark Tn and memory space 204 stores image 210 marked with time Tn+1. The time designations Tn and Tn+1 may be time marks that represent the time mark at which the respective image occurred within the stream of ultrasound images generated by probe 220. In one embodiment, the video module 219 marks each image in the data stream from probe 220 with a time mark indicating the time the image was generated by the probe 220. The image comparator module 214 may access the memory spaces 202 and 204 via data path 222 and may compare the two sequential images 208 and 210. In one embodiment, the image comparator module 214 analyzes the two sequential in time images 208 and 210 to detect changes between the images and determine whether images captured by the probe 220 are changing over time. Changes in the images over time may indicate that the probe 220 is in use by the clinician and conversely a lack of changes in the images as time passes may indicate that the clinician has suspended use of the probe 220, and the system may be placed in a low-power mode.

To detect changes between the images 208 and 210, the image comparator module 214 may execute any suitable image comparison program process capable of comparing two or more images and determining differences between those images. In one embodiment, the image comparator module 214 performs an edge detection and comparison procedure to determine whether similar edges in the images 208 and 210 are changing location. The image comparator module 214 first performs edge detection and then compares the location of the detected edges in image 208 against the location of the edges detected in image 210. Locations of edges may, in some embodiments, be understood as the (x,y) pixel coordinate of an edge within the image data. If the images 208 and 210 have edges in different locations, the image comparator module 214 may determine that the images 208 and 210 are different and these differences indicate the probe 220 is in use during the time period of this image sequence. In another embodiment, the image comparator module 214 compares the images 208 and 210 on a pixel-by-pixel basis, comparing the grayscale value of each pixel in image 208 against the grayscale value of the corresponding pixel in image 210. For example, a pixel (Xn, Ym) in image 208 may be compared against pixel (Xn, Ym) in image 210. In this embodiment, video module 219 stores the images captured by probe 220 as grayscale images, often referred to as black and white images. Each pixel in a stored image is given a grayscale value. For a grayscale image, the grayscale value is typically a single number that represents the brightness of the pixel. In one embodiment, the pixel value is stored as a data byte, in some examples as an 8-bit integer giving a range of values from 0 to 255. The image comparator module 214 compares the grayscale value for each pixel in image 208 against the grayscale value for the corresponding pixel in image 210 and identifies the difference between the two grayscale images. The image comparator module 214 may have a threshold difference value, such as 10 or 25, where that threshold difference value must be exceeded before the pixel value of image 208 is identified as different from the corresponding pixel value in image 210. This threshold difference value can be used to address the typical noise that occurs in an ultrasound image. That noise may create differences in pixel values but does not represent differences between the images 208 and 210 arising from a clinician using the probe 220 in the procedure. The image comparator module 214 may compare each pixel of image 208 against the corresponding pixel in image 210, and record for each pixel pair the amount, if any, of difference above for that pixel pair. The image comparator module 214 may generate a summation of the differences to determine a total difference value representative of the difference in grayscale values between the pixels of image 208 and the pixels in image 210. If the total pixel value difference is above a particular total difference threshold, such as for example a total difference threshold of 2000, the image comparator module 214 may determine that differences have been detected between the images 208 and 210. Alternatively, if the total pixel value is less than the total threshold value, the image comparator module 214 may determine that the images 208 and 210 are not different.

As further depicted in FIG. 2, the application 206 includes the timer module 212. The timer module 212 communicates time information to the power control module 218 and acts as a timer function that operates to count down from a timeout period, for example 30 seconds or 90 seconds or some other timeout period that is suitable for the procedure being carried out by the clinician. That timer module 212 has a reset input that connects to the image comparator module 214 via the data path 216. The image comparator module 214 may transmit a reset signal via path 216 from the image comparator module 214 to the timer module 212.

In one embodiment, the image comparator module 214 compares images 208 and 210 and determines if the images are different. If the images 208 and 210 are different, the image comparator module 214 activates the reset function and transmits via path 216 a reset signal to timer module 212. The reset signal directs the timer module 212 to reset the timeout period to the full timeout period. Alternatively, if the image comparator module 214 determines that the images are not different according to the criteria being applied, the image comparator module 214 may continue to compare successive images. To this end, the image comparator module 214 may use data path 222 to store at memory spaces 202 and 204, the next pair of subsequent images to compare, such as for example images Tn+1 and Tn+2. In one embodiment the image comparator module 214 continues to compare successive images. Each time the image comparator module 214 detects a change between the images that meets the threshold set to indicate a change suggesting the probe is in use, the image comparator module 214 will reset the timer module 212. If the image comparator module 214 fails to find a difference in the image sequence during the timeout period being countdown by the timer module 212, the image comparator module 214 will not reset the timer module 212 as the timer module 212 counts down until expiration of the predetermined and set time. If the timer module 212 counts down to expiration of the predetermined and set timeout period, such as for example 90 seconds or 20 seconds, the timer module 212 issues an instruction via path 217 to the power control module 218. The instruction from timer module 212 directs the power control module 218 to place the system 200 into a low power mode. Additionally, the power control module 218 transmits an instruction via data path 213 to the reconfiguration module 215 to reconfigure the UI control button 230 to operate as a control to release the system 200 from the low-power mode. In the depicted embodiment the data path 224 is a bi-directional path. In one embodiment, the instruction to the reconfiguration module 215 to reconfigure the UI control button 230 to operate as a release from low-power mode may also cause the reconfiguration module 215 to send an instruction over path 224 to have the probe 220 enter a low-power mode. As discussed above, this may cause the probe 220 to reduce the power and voltage delivered to the transducer head 106 (e.g., to a chip including transducers and circuitry in the transducer head 106). Additionally, the application 206 may cause the handheld device 225 to enter a low-power mode, thus having both the handheld device 225 and the probe 220 in a low-power mode.

When the power control module 218 has placed the system 200 into a low-power mode, the reconfiguration module 215 monitors the UI control button of probe 220 via the path 224. If the clinician activates the UI control button 230, an instruction is passed to the reconfiguration module 215. The instruction directs the reconfiguration module 215 to send an instruction via data path 213 to the power control module 218 to release the system 200 from the low-power mode and place the system 200 into a power mode suitable for imaging operations. In one optional embodiment, the reconfiguration module 215 then operates the UI control button 230 as an image capture button that will cause the video module 219 to grab an image from the image stream on data path 226 and will record that image to a capture reel stored in data memory 203, or operates the UI control button 230 for other functions such as, but not limited to, making battery status readings, performing imaging control such as for controlling depth, controlling gain, switching modes, turning color on and/or off, controlling a wireless pairing process, or for soft resetting of the probe. In other embodiments, the reconfiguration module 215 then operates the UI control button 230 as a probe battery indicator that will cause the video module 219 to display on handheld device 225 an indication of the amount of power left in the probe battery. In other embodiments, the reconfiguration module 215 may reconfigure the UI control button for other operations. The reconfiguration module 215 can perform image control of video module 219 such as turning color on and/or off via data path 223.

In one embodiment, the handheld device 225 can display on its screen a graphic image indicating visually that the system 200 is transitioning from low-power mode to a power mode suitable for imaging. Once the system 200 is in a power mode suitable for imaging the handheld device 225 can provide a visual indicator to the clinician that the system 200 is ready for imaging operations and the clinician so can use probe 220 to generate a stream of ultrasound video data images. One such visual indicator is depicted in FIG. 1 as the icon 120. In one embodiment, when the power control module 218 has placed the system 200 in low-power mode, the power control module 218 may cause the handheld device 225 to provide a visual indicator that the system 200 is in a low-power mode. For example, the power control module 218 may direct the handheld device 225 to create a yellow block and present that block as the icon 120 depicted in FIG. 1. Once the power control module 218 has released the system 200 from low-power mode and has begun transitioning the system 200 to a power mode suitable for imaging, the power control module 218 may instruct the system 200 to display within the icon 120 a visual indicator such as an orange block that indicates the system 200 is in a transition period between power modes. Once the power control module 218 has transitioned the system 200 to a power mode suitable for imaging, the power control module 218 may cause the handheld device 225 to display a visual indicator, such as a green block, within the icon 120. The green icon 120 indicates to the clinician that the system 200 is ready for imaging operations and use of the UI control button 230 will cause the probe 220 to capture image data for display on the handheld device 225, or to activate various functions such as, but not limited to, making battery status readings, performing imaging control such as for controlling depth, controlling gain, switching modes, turning color on and/or off, controlling a wireless pairing process, or for soft resetting of the probe.

Figure 3:
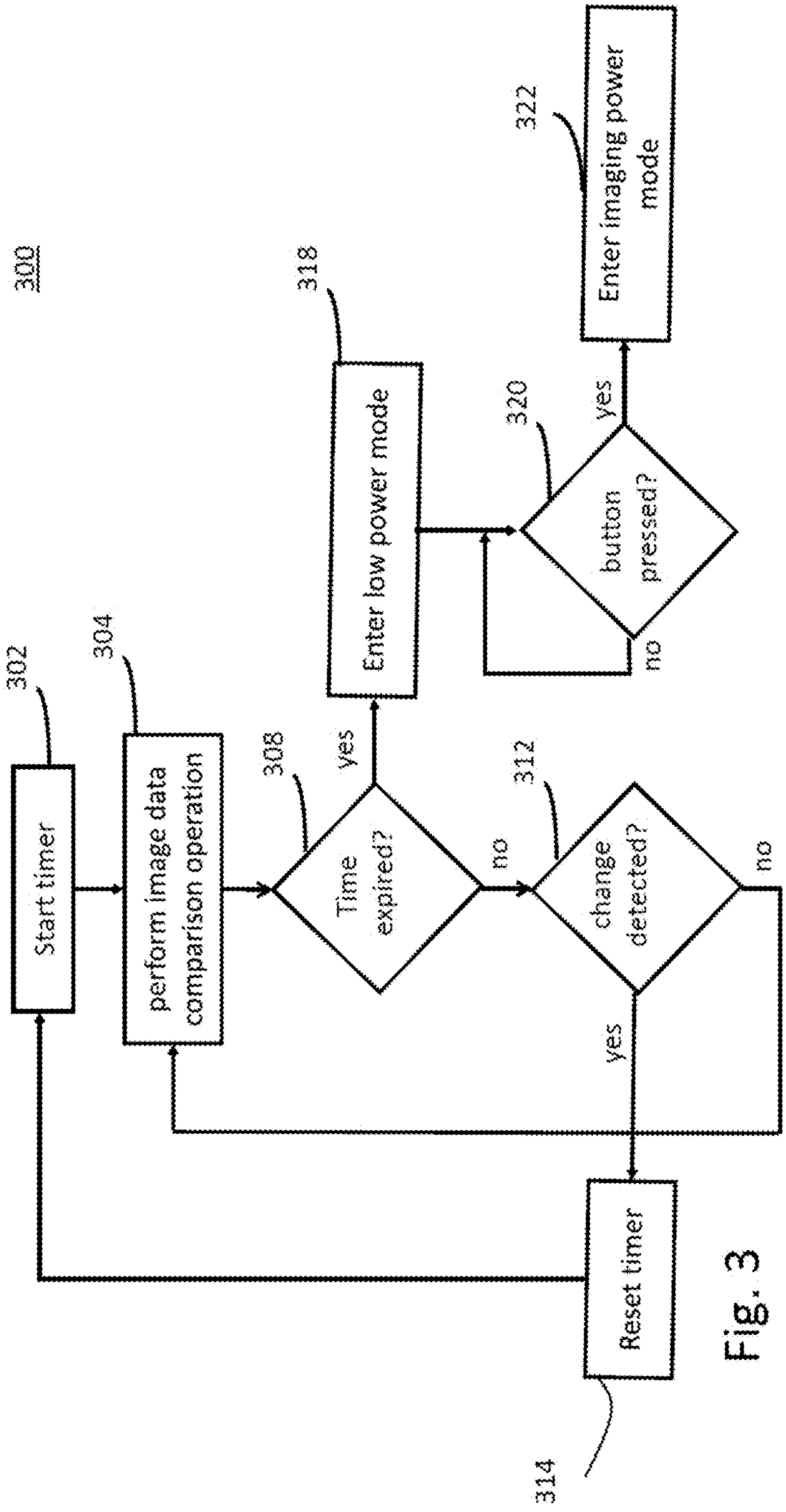
FIG. 3 is a flow chart of one embodiment of the methods described herein.

FIG. 3 depicts another aspect of the systems and methods described herein which is a process 300 capable of being executed on a handheld device and capable of transitioning that handheld device from a low power mode to a mode suitable for imaging and conversely from a mode suitable for imaging to a low power mode. In one practice, the low-power mode will conserve energy and reduce thermal output of an ultrasound imaging system. In particular FIG. 3 depicts a process 300 that begins at 302 which sets a timer. The timer may be any typical timer of the type that will countdown from a predetermined and set timeout period such as a stored timeout period of 90 seconds, 30 seconds, 20 seconds or any timeout period that is suitable for the application being addressed. The application being addressed will typically be an imaging study being carried out by the clinician. Some of those imaging studies will lend themselves to timeout periods that are longer, such as 90 seconds, and in some cases the timeout period will be shorter, such as 20 seconds, and the timeout period that is more right for a particular study may be stored as the preset timeout parameter. In one example, the timeout period may be a time duration associated with a preset imaging procedure, such as an imaging study for a carotid artery study. In the process 300, the timeout period may be selected to set a time period during which images are expected to change as long as the clinician has the ultrasound system in use for the carotid artery study. If images are not changing for 30 seconds or more, the clinician may have suspended use, and entering a low-power mode to reduce consumption and heat may be a benefit to the patient. In another example, a preset may be for a needle visualization study. The preset for this type of study, which can take more time to perform than a carotid artery study, may be a longer duration such as 90 seconds. In still another example, the process 300 may set the timer to a default timeout period of 30 seconds. The process 300 in 302 may use the default timeout unless a timeout associates with a selected preset is available.

From 302 the process 300 proceeds to an image data comparison operation in 304. The image data comparison operation can be any of the image data comparison processes that are suitable for comparing two images generated by an ultrasound probe to determine whether there are differences between the two images. In the process 300 after two successive images are compared the process 300 proceeds to 308 where the process 300 determines whether the time period set in 302 has expired. If the timeout period has expired the process will place the system into a low-power mode in 318. Alternatively, if the timeout period has not expired, the process 300 will proceed to 312 and determine whether a change was detected in the images. If there was a change detected in the images, the process 300 determines that time has not expired, and a change between images has been detected and therefore the system should proceed to 314 wherein it resets the timer to start the timer for the full timeout period. After 314 the timer is reset and the process 300 begins again at 302. Alternatively, if in 312 no change is detected between the images, the process 300 will proceed to 304, collect a subsequent sequence of images and begin the image data comparison operation over again.

Returning to 308 if the timeout period has expired the process 300 will proceed to 318 and enter the system into the low-power mode. From 318, the process 300 proceeds to 320 where the process 300 continually monitors the UI control button to determine whether it has been activated by the clinician. If the UI control button has not been activated, the system loops continuously as shown in FIG. 3 to continue to look whether the clinician has activated the button. Once the button has been activated, the process 300 proceeds to 322 wherein the system transitions to an imaging power mode which is a power mode suitable for allowing the clinician to take images. At that time, the UI control button on the probe will be configured as an image capture user interface control button for capturing images to store in data memory, or for other functions such as, but not limited to, making battery status readings, performing imaging control such as for controlling depth, controlling gain, switching modes, turning color on and/or off, controlling a wireless pairing process, or for soft resetting of the probe.

Figure 4:
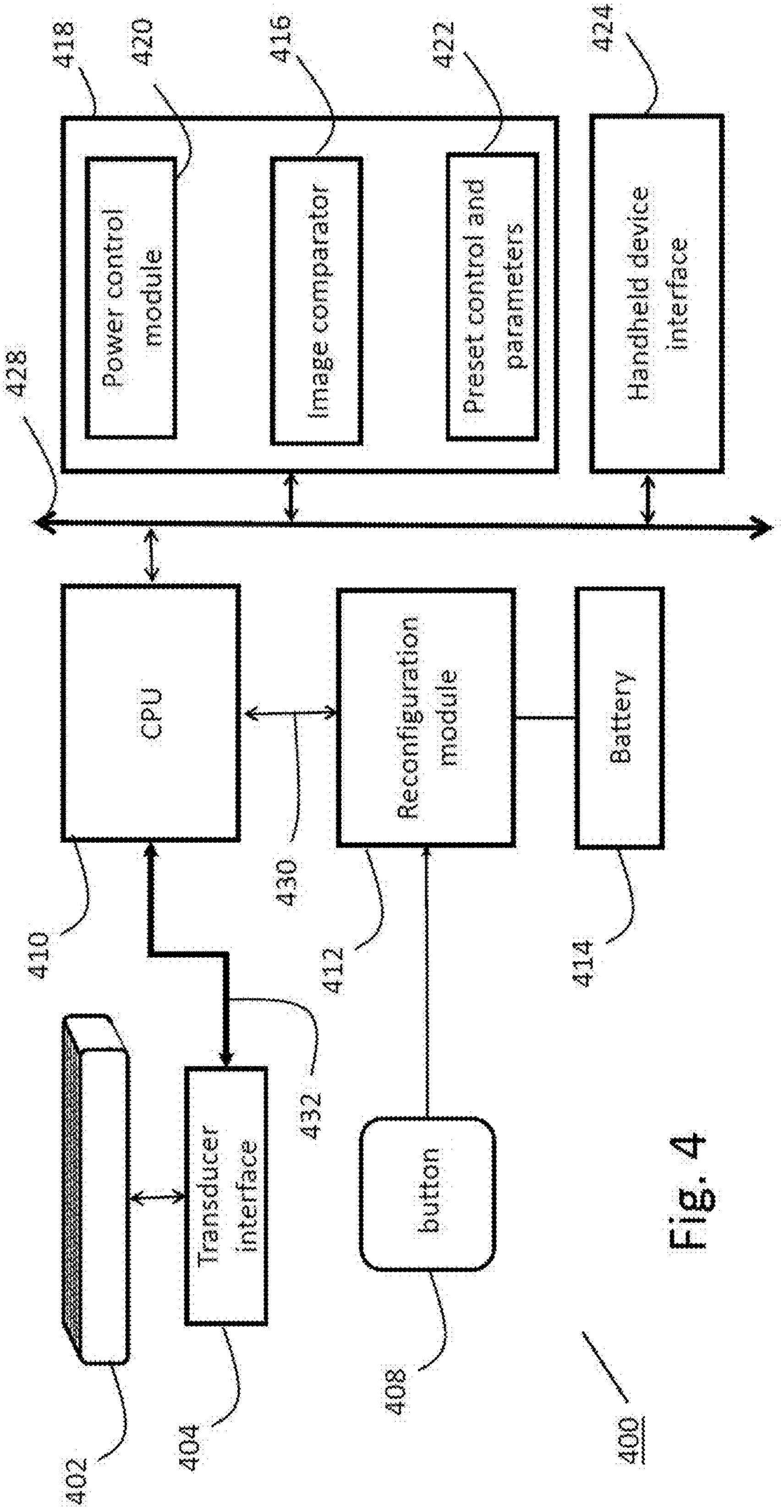
FIG. 4 is an exploded view of one alternative embodiment of a probe that controls transitions between a low-power mode and a power mode for imaging.

FIG. 4 depicts an alternative embodiment of the systems described herein. In particular, FIG. 4 depicts an exploded view of a probe 400 that has a reconfiguration module 412 built into the probe 400 to allow the probe 400 to control the response to the activation of the UI button 408 and to transition a system, such as the system 100 of FIG. 1, between a low-power mode and a power mode suitable for imaging operations. In particular, FIG. 4 is an exploded view of a probe 400 having a transducer head 402 that may include the chip discussed above having transducers, amplifiers, A/D converters, and other circuitry, a transducer interface 404 to interface the transducer head chip with the CPU 410 of the probe 400, the UI button 408, a processing unit, which in the depicted embodiment is the CPU 410 but may also be a FPGA, a signal processor, or a combination thereof, a reconfiguration module 412, a battery 414, a memory unit 418 storing an image comparator module 416, a power control module 420 and a preset control and parameter memory 422, and a handheld device interface 424. Additionally, FIG. 4 depicts a bus 428 that allows the CPU 410, the memory unit 418 and the handheld device interface 424 to exchange information. In the depicted probe 400 the transducer interface 404 couples directly to the transducer 402 through a dedicated path. Additionally, the transducer interface 404 includes a dedicated path 432 to the CPU 410. In alternate embodiments the transducer interface 404 could use the bus 428 to transfer data rather than a dedicated data path. The depicted UI button 408 has a direct connection to the reconfiguration module 412 and the reconfiguration module 412 has a data path to the CPU 410 depicted by bidirectional data path 430. Again, in alternate embodiments the reconfiguration module 412 could use the bus 428 to exchange data with the CPU 410. Those of skill in the art will know that different circuit board layouts and different hardware and software architectures may be used with the systems described herein and the layout and architecture used will typically depend upon the form factor, chip set used and other factors such as cost. However, any suitable architecture may be used.

The UI button 408 may be a mechanical button that responds to a force applied by the clinician. When the force is applied to UI button 408 it activates and generates a control signal that is passed to the reconfiguration module 412. As such, the UI button 408 acts as a UI that collects a command representing activation of the UI button 408 by the user and generates a signal representative of that command and passes that signal to the reconfiguration module 412.

The power control module 420 may, in one embodiment, activate a low-power mode to reduce power consumed by the probe 400 and optionally by a handheld device that will interface to the probe 400 via the handheld device interface 424. For ease of illustration, the handheld device that connects to handheld device interface 424 is not shown in FIG. 4 but it may be similar to the handheld device 108 of FIG. 1. The power control module 420, in certain embodiments performs the auto-freeze function discussed above. To this end, the power control module 420 monitors the use of the imaging device and enters the imaging device into a low-power mode if use has been suspended for a predetermined and set timeout period, such as for example ninety seconds. To monitor whether the use of the imaging device has been suspended, the power control module 420 may include sensors such as accelerometers, gyroscopes, magnetometers or other motion sensors, movement that can detect whether the clinician is moving the probe 400. Additionally, the power control module 420 may monitor whether the clinician is activating the UI button 408 to capture images. In further optional embodiments, the handheld device interface 424 communicates with a handheld device, such as the handheld device 108 of FIG. 1, and queries the handheld device 108 to determine if the handheld device 108 is being used to enter commands or review data.

Additionally, in some embodiments, the power control module 420 is responsive to the image comparator module 416. The image comparator module 416 compares the sequence of images generated based on signals received by the transducer head 402, to determine whether changes have occurred between two or more successive images. The process for comparing images may be include the processes disclosed above with reference to FIG. 2. If the image comparator module 416 fails to detect that images have changed during the timeout period, the image comparator module 416 can provide a signal to the power control module 420 and the power control module 420 may put the probe 400 and/or the handheld device 108 in a low-power mode.

To this end, the power control module 420 may implement a countdown timer that is set for a timeout period. Once the timeout period has expired if no activities have occurred representing use of the device by the clinician, the power control module 420 may determine that use of the system 100 has been suspended and may place the system 100 into the low-power mode. Once in the low-power mode, the power control module 420 may generate a wake-up configuration signal representative of a command to reconfigure the UI control button 408 to operate as a power mode control. In the embodiment depicted in FIG. 4, the power control module 420 generates the wake-up configuration signal and communicates that signal via data bus 428 to the CPU 410 and the CPU 410 provides the wake-up configuration signal to the reconfiguration module 412. The reconfiguration module 412 may receive the wake-up configuration signal and reconfigure the UI button 408 to operate as a control for transitioning the probe 400 and/or handheld device 108 out of the low-power mode and into a power mode suitable for imaging operations. This typically will have the handheld device 108 and/or the probe 400 increase power consumption to a level sufficient to support ultrasound imaging operations.

In some embodiments, placing a device into a low-power mode includes activating a transistor switch to reduce the current and/or voltage delivered to components of the device. In one embodiment, the power control module 420 may activate a switch to reduce current and/or voltage delivered to the transducer head 402, which as discussed above may include CMUTs or PMUTs, amplifiers and converters. Additionally, the power control module 420 may reduce power consumed by CPUs, FPGAs and signal processors. For example, certain CPUs have on board sleep-modes that have internal power transistor switches that turn off the current delivered to certain other transistors in the CPU. This reduces the power consumed by the CPU, although it deactivates any of the functions of the CPU that had been provided by the transistors that are now turned off. Once the transducer head 402 and other elements, such as CPUs, FPGAs and signal processors, are in a power mode for imaging operations, the power control module 420 may issue a wake-up configuration signal to the reconfiguration module 412.

The reconfiguration module 412 monitors the UI button 408 and determines if the UI button 408 is activated. The reconfiguration module 412 will respond to an activation signal from the activated UI button 408 based on how the reconfiguration module 412 is configured to respond. For example, when the reconfiguration module 412 receives the wake-up configuration signal from the power control module 420, the reconfiguration module 412 is configured to operate the UI button 408 as a control to have the handheld device 108 and the probe 400 consume power sufficient to perform imaging operations. Alternatively, if the power control module 420 has sent the reconfiguration module 412 an imaging configuration signal, the reconfiguration module 412 will be configured to perform imaging operations, or indicate battery power, or provide some other operation. These other operations are typically of the type that cannot be performed in a low-power mode and require that the probe 400 and handheld device 108 to be in a power mode suitable for imaging operations. In the embodiment depicted in FIG. 4, the power control module 420 is shown as a separate module from the reconfiguration module 412 and the power control module 420 includes the functions for detecting whether the probe 400 or handheld device 108 are in a low-power or "sleep-mode". However, it will be apparent to those of skill in the art that in alternate embodiments, the reconfiguration module 412 may optionally include some of the functions for detecting the power mode of the device. For example, it may be that the clinician may employ a user interface control to place the device 400 into a low-power mode to conserve power and reduce heat output. In other alternative embodiments, the battery 414 has a low power detector that places the probe 400 into a low power mode. In such embodiments, the power control module 420 or the reconfiguration module 412 may include a power mode detection circuit that detects the power mode of the probe 400 to determine whether the probe 400 is operating in a low-power mode. In still other embodiments, the power control module 420 or the reconfiguration module 412 in FIG. 4 may couple to the battery 414 and monitor the battery 414 to determine whether the battery power output is at a level that indicates the probe 400 is in a low-power mode, or a power mode suitable for imaging operations. Accordingly, it will be understood by those of skill in the art that FIG. 4 depicts one example embodiment of the systems described herein and other embodiments employing different arrangements and organizations of functions will be readily realized and all such embodiments are encompassed by this disclosure.

In operation, the reconfiguration module 412 multiplexes the activation signal from the UI button 408 based, at least in part, on the power mode of the device 400. In the embodiment depicted in FIG. 4, the reconfiguration module 412 is a logic circuit that detects the button activation signal indicating that the clinician has activated the button 408. In this embodiment, the button 408 generates a transistor level signal of the type that can be received by a digital logic device such as a CMOS circuit. In one embodiment, the reconfiguration module 412 is a CMOS circuit that detects the activation signal from the UI button 408 and generates a response based on a configuration signal from the power control module 420. If the power control module 420 has issued an imaging configuration signal, the reconfiguration module 412 may respond to the activation signal from the UI button 408 and generate an image capture signal and pass that signal via bidirectional path 430 to the CPU 410. The CPU 410 may respond to that image capture signal to capture an image to present to the clinician, such as by presenting the image in the image window 110 depicted in FIG. 1, or the reconfiguration module 412 may respond to the activation signal from the UI button 408 to activate various other functions such as, but not limited to, making battery status readings, performing imaging control such as for controlling depth, controlling gain, switching modes, turning color on and/or off, controlling a wireless pairing process, or for soft resetting of the probe.

Alternatively, if the power control module 420 has issued a wake-up configuration signal to the reconfiguration module 412, the reconfiguration module 412 may generate a wake-up signal and pass that signal to the CPU via path 430. The CPU 410 may respond to the wake-up signal by releasing the probe 400 from the low-power mode and placing the probe 400 into the imaging power mode and further optionally and additionally causing the system 100 to capture an image for display to the clinician or activate another function such as, but not limited to, making battery status readings, performing imaging control such as for controlling depth, controlling gain, switching modes, turning color on and/or off, controlling a wireless pairing process, or for soft resetting of the probe.

In further embodiments, the CPU 410 may issue a wake-up signal to a handheld device via the handheld device interface 424. This will instruct the handheld device to transition from low-power mode to a power mode suitable for imaging.

In operation, the clinician can use the UI button 408 on the device 400 to control both imaging operations and power control, thereby reducing the need to have the clinician monitor the power state of the device 400 during operations and reducing the need to have additional control buttons built onto the device 400 or additional control buttons presented within the UI window 112 on the handheld device 108. The inventors recognized that the handheld device 108 may not meet sterility protocols and as such having a control button on the handheld device 108 that the clinician must operate is a burden as it requires the clinician to follow a sterility protocol due to touching a control button presented on the non-sterile UI window 112.

Figure 5:
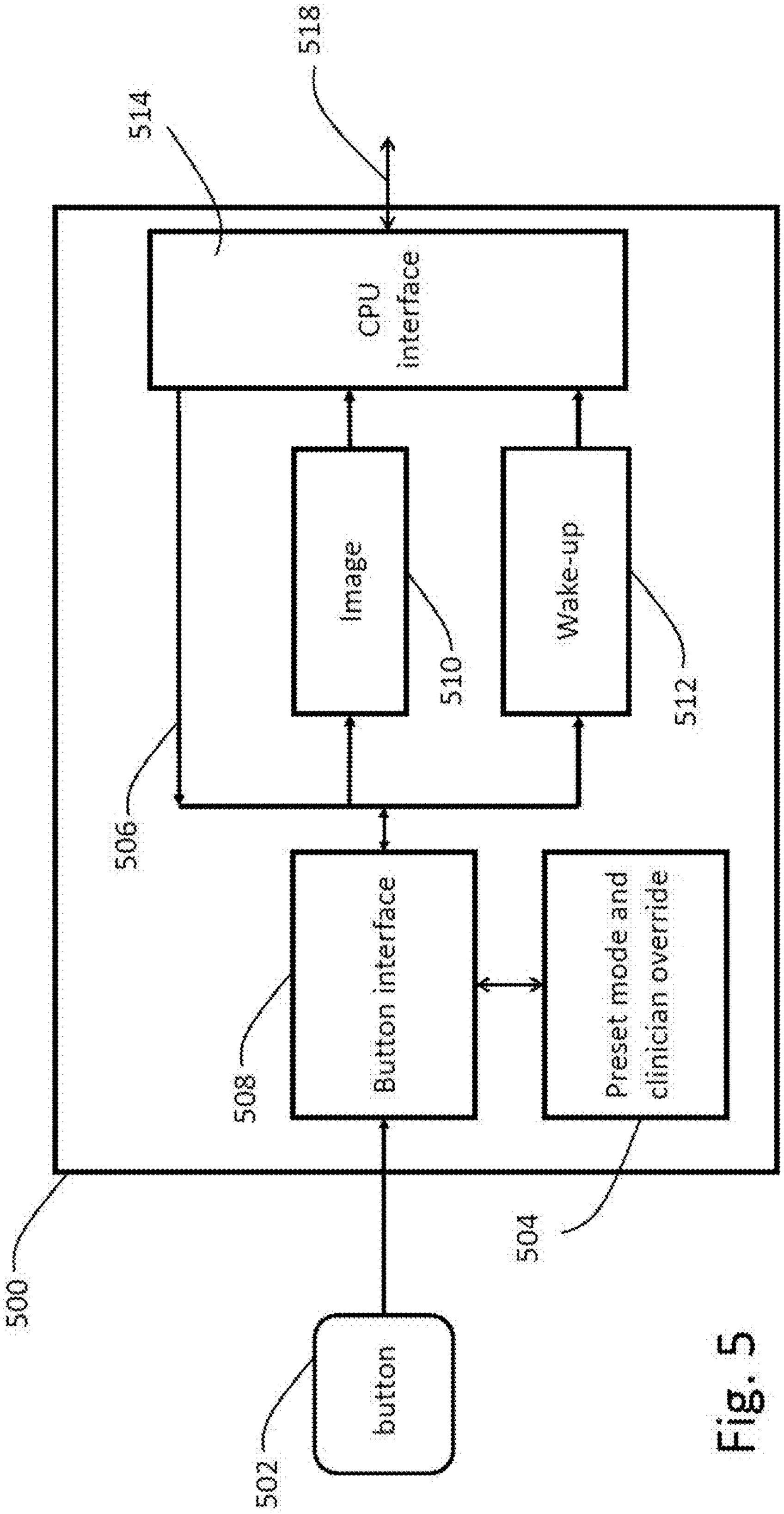
FIG. 5 a schematic block diagram of a reconfiguration module of the type suitable for use in the system illustrated in FIG. 4.

FIG. 5 depicts in more detail one embodiment of a reconfiguration module such as the reconfiguration module 412. In particular, FIG. 5 depicts a reconfiguration module 500 that couples to the UI button 502. The reconfiguration module 500 couples to the UI button 502 so that the button interface circuit 508 receives the activation signal from UI button 502. The reconfiguration module 500 includes a button interface circuit 508 as well as an image control signal generator 510, a wake-up signal circuit 512, a memory 504 for storing preset and clinician override parameters and a CPU interface 514 that can pass signals to the CPU 410 via the bidirectional data path 518 and which can pass signals to the button interface via the data path 506.

In operation, the UI button 502 generates the activation signal which is passed to the button interface circuit 508. The button interface circuit 508 can be CMOS logic that receives the activation signal. As further depicted, the button interface circuit 508 may also connect to the CPU interface 514 via data path 506 to receive the wake-up configuration signal from the power control module 420. The wake-up configuration signal may configure that button interface logic 508 to respond to the UI button activation signal as a wake-up control. To that end, the button interface 508 will generate a wake-up signal by sending an activate signal to the wake-up circuit 512. The wake-up circuit 512 will generate the wake-up signal that can be delivered through the CPU interface 514 to the CPU 410. The wake-up signal in some embodiments is a digital data command transferred over a data bus, such as the data path 430, to the CPU 410 and in some embodiments, it is an interrupt signal sent to the CPU 410. However, any suitable form of wake-up signal may be employed with the systems and methods described herein.

In the embodiment described with reference to FIG. 4, the CPU 410 may respond to the wake-up signal by executing a program module, which can be a set of software instructions such as the power control module 420 depicted in FIG. 4. The power control module 420 will recognize that the system 100 is in a low-power mode and that a wake-up signal has been issued by the clinician pressing the UI control button 408. The power control module 420 will generate the signals to bring the system 100 out of its low-power state and into a power state suitable to have the system 100 perform imaging operations. At that time the clinician can receive a signal on a display such as the UI window 112. The signal within the UI window 112 may let the clinician know that the system 100 which had been in a low-power, sometimes called a "sleep" mode or "auto-freeze" mode, is now in a power mode or is preparing to enter a power mode that is suitable for imaging operations. Once the system 100 enters a power mode capable of supporting imaging operations, the clinician may again activate the UI button 408 and the UI button 408 will generate an activation signal that passes to button interface circuit 508.

Returning to FIG. 5, if alternatively, the button interface circuit 508 has received an imaging configuration signal via data path 506, the button interface logic 508 will activate the image control signal generator 510. The image control signal generator 510 will generate an image control signal that passes through CPU interface 514 onto the bidirectional path 518 for the CPU to act upon. The CPU can receive the image control signal and respond to the image control signal by implementing a set of instructions stored in memory. In one embodiment, those instructions will cause the system to begin imaging operations and present the images generated by the probe on the handheld device 108, typically within the image window 110.

In optional embodiments, the systems described herein may be responsive to the type of imaging operation that the clinician is undertaking. In certain imaging devices, such as those described in U.S. Pat. No. 10,709,415 assigned to the assignee hereof, the probe 102 may be placed into a preset. Table 1 below lists certain example presets.

| Preset |
|---|
| Abdomen |
| Abdomen Deep |
| Aorta & Gallbladder |
| Bladder |
| Cardiac |
| Cardiac Deep |
| Coherence Imaging |
| FAST |
| Lung |
| MSK-Soft Tissue |
| Musculoskeletal |
| Nerve |
| OB 1/GYN |
| OB 2/3 |
| Ophthalmic |
| Pediatric Abdomen |
| Pediatric Cardiac |
| Pediatric Lung |
| Small Organ |
| Vascular: Access |
| Vascular: Carotid |
| Vascular: Deep Vein |

T Each preset is a mode adapted for a particular type of imaging study. Presets may help with imaging studies and may be employed within systems that have the auto-freeze feature described herein, but optionally, presets may be employed within systems that do not have such an auto-freeze feature. Some of these presets are used with procedures that benefit from a sterility protocol. In some embodiments, the systems described herein are, at least in part, responsive to the preset. For example, for the embodiment of FIG. 2, a preset parameter memory 232 is provided to store data representative of a current preset selected by the clinician. Similarly, the embodiment of FIG. 5 depicts a reconfiguration module 500 having a memory 504 that stores data representative of a current preset selected by the clinician.

If the data stored in a preset parameter memory represents a preset that is associated with a sterility protocol, then the system described herein may reconfigure the UI button responsive to the stored preset data. For example, if the data stored in preset parameter memory 504 represents a preset that is associated with a sterility protocol, then the button reconfiguration module 500 will reconfigure the UI button 502 to generate a wake-up control signal to remove the device from a low-power mode when the UI button 502 is activated. For example, such presets that may be associated with a sterility protocol may include the presets of Vascular Access, Nerve, MSK, MSK Soft Tissue, Small Organ, Vascular Deep Vein, Vascular Carotid, and Face presets. Additionally, in veterinary applications, presets that may be associated with a sterility protocol may include Vascular and Bladder presets for a veterinarian probe. Similarly, for the embodiment of FIG. 2, if the data in preset parameter memory 232 represents a preset that is associated with a sterility protocol, then the reconfiguration module 215 will reconfigure the UI control button 230 to generate a wake-up control signal to remove the device from a low-power mode when the UI control button 230 is activated In this way, the systems described herein provide the clinician with a sterile UI button that can remove the device from a low-power mode during procedures that benefit from sterile conditions. Alternatively, the data in the preset memory may represent a preset for a procedure that is typically performed without instituting a sterility protocol. In that case, the reconfiguration module 500 or reconfiguration module 215 may respond to that "non-sterile" preset data by maintaining its respective UI button as configured, such as for example for image capture or for indicating battery power levels, or some other operation such as, but not limited to, performing imaging control such as for controlling depth, controlling gain, switching modes, turning color on and/or off, controlling a wireless pairing process, or for soft resetting of the probe.

In such embodiments, if the device is in a low-power mode during a non-sterile preset imaging study, the clinician may need to activate a software switch on the display of the handheld device to release the device from the low-power mode.

In optional embodiments, the memories 232 or 504 may further store data representative of a clinician instruction to override the reconfigure operation of reconfiguration module. In this optional embodiment, an application executing on the handheld device may provide the clinician with software switches that the clinician can use to override the reconfiguration operation of reconfiguring the UI button to act as a wake-up control by storing a clinician override data signal in memory 232 or 504. The respective reconfiguration module can check the override data signal stored in memory and if the clinician has instructed the reconfiguration module to override the reconfiguration the respective UI button, the reconfiguration module will not operate to reconfigure the operation of the UI button and that button will, typically, continue to act as an image capture button or a battery power indicator button or a button for some other functions such as, but not limited to, making battery status readings, performing imaging control such as for controlling depth, controlling gain, switching modes, turning color on and/or off, controlling a wireless pairing process, or for soft resetting of the probe.

In a further optional embodiments, the clinician may override the preset parameter described above and require the reconfiguration modules 215 and 500 to reconfigure the respective UI control button 230 and 502 for all operations regardless of the stored preset data. Thus, the clinician can require the reconfiguration modules 215 and 500 to reconfigure the UI button to act as a wake-up control button for when the device is in a low-power mode for all operations and procedures. The reconfiguration modules 215 and 500 will be responsive to the clinician override data and will reconfigure the operation of the UI button regardless of whether the stored preset parameters in memory 232 and 504 are associated with a sterile procedure.

Figure 6:
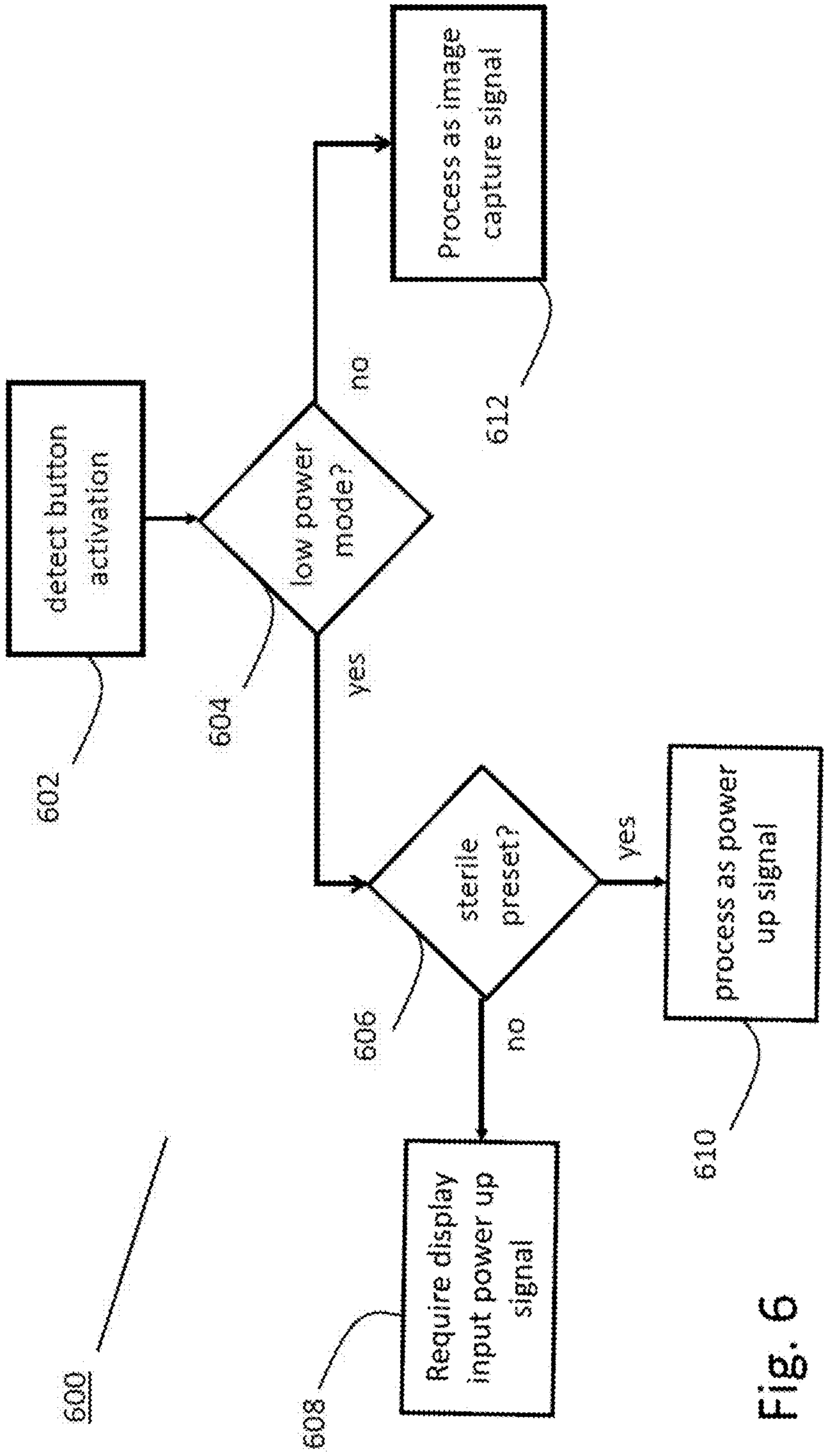
FIG. 6 is a flow chart of one embodiment of the methods described herein.

FIG. 6 depicts an embodiment of one process that may be used with the systems described herein, for providing a UI button that reconfigures the interface based, at least in part, on the power mode of the imaging device and on whether a preset indicates a sterile procedure is indicated. In particular, FIG. 6 depicts a process 600 that begins in 602 where the process 600 detects that a UI button has been activated. If a UI button has been activated and an activation signal is being presented to the process 600, the process 600 proceeds to 604 where the process 600 determines whether the device is in a low-power mode. A low-power mode can be any low-power mode such as a sleep-mode for the CPU, a low-power mode for the transducer head 106, a low-power mode instituted by an auto-freeze operation initiated by the power control module 218 or any suitable low-power mode used to either conserve power or reduce thermal output, or for any typical reason used by such handheld imaging devices.

If the device is in a low-power mode, the process 600 proceeds from 604 to 606 wherein the process 600 checks whether the device is in a preset often used for a sterile operation. To this end, the process 600 may check the preset parameter memory (232, 504). If the device is in a preset for a sterile operation the process 600 proceeds from 606 to 610 to generate a power-up signal of the type capable of moving the device from a low power state to an operational power state suitable for imaging. Alternatively, if in 606 the process 600 determines that the device is not in a preset or is in a preset that does not indicate sterile operation, the process 600 proceeds from 606 to 612 where, in one embodiment, an image capture signal may be generated to capture an image for display within the image window 110 on the handheld device 108. In alternate embodiments, process, 612 may generate other signals for other functions such as indicating battery power level, or any other function that the UI button may be configured to activate, such as, but not limited to, making battery status readings, performing imaging control such as for controlling depth, controlling gain, switching modes, turning color on and/or off, controlling a wireless pairing process, or for soft resetting of the probe.

Returning to 604, if the process 600 determines in 604 that the device is not in a low-power mode but is instead in a mode suitable for performing an imaging operation the process 600 can proceed from 604 to 612 where, in one embodiment, an image capture signal may be generated to capture an image for display within the image window 110 on the handheld device 108. In alternate embodiments, process, 612 may generate other signals for other functions such as indicating battery power level, or any other function that the UI button may be configured to activate, such as but not limited to, making battery status readings, performing imaging control such as for controlling depth, controlling gain, switching modes, turning color on and/or off, controlling a wireless pairing process, or for soft resetting of the probe.

Figure 7:
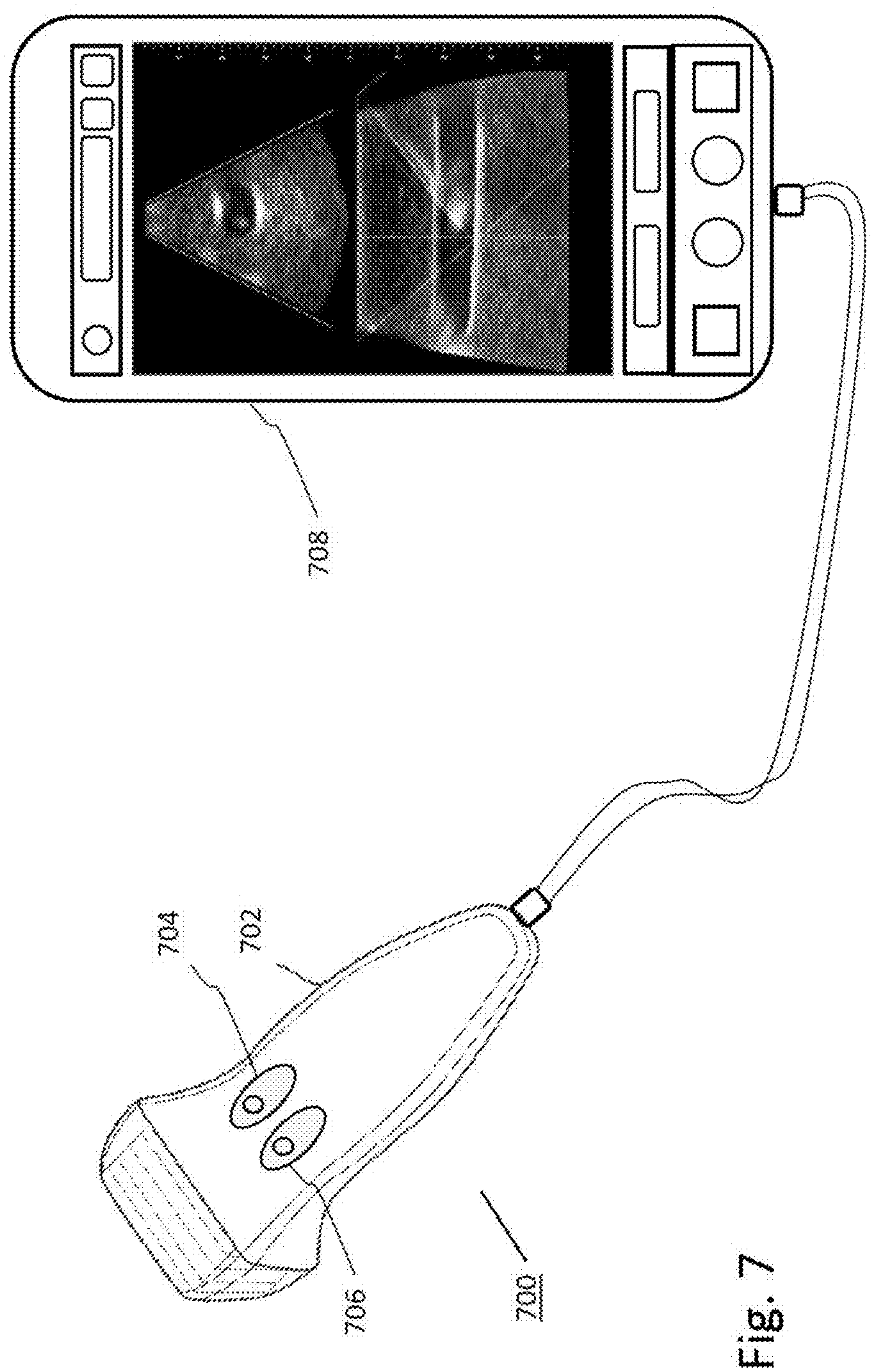
FIG. 7 depicts an alternative embodiment of the systems described herein wherein the depicted probe has plural UI buttons.

FIG. 7 depicts an alternative embodiment of a system 700 of the type described herein. In this embodiment the probe 702 has a plurality of UI buttons 704 and 706. The clinician may program one of the UI buttons 704 or 706 to control the power-up feature described above to move the system 700 from a low-power mode to an operational power-mode. In this embodiment, an application running on the handheld device 708 can present to the clinician a software switch that allows the clinician to select either, or in some embodiments both, of the UI buttons 704 and 706. The button selected by the clinician will have its activation signals processed by the reconfiguration module (215, 500). In this embodiment, the clinician has programmable control over the whether the UI button will be processed by the reconfiguration module and can, for example, set UI button 704 for one preset and the other UI button 706 for a different preset.

The systems and methods described herein reference circuits, CPUs and other devices, and those of skill in the art will understand that these embodiments are examples, and the actual implementation of these circuits may be carried out as software modules running on microprocessor devices and may comprise firmware, software, hardware, or any combination thereof that is configured to perform as the systems and processes described herein. Further, some embodiments may also be implemented by the preparation of application-specific integrated circuits or by interconnecting an appropriate network of conventional component circuits. To illustrate this interchangeability of hardware and software, various illustrative components, blocks, modules, circuits, and steps have been described herein generally in terms of their functionality. Whether such functionality is implemented as hardware or software depends upon the application and design constraints imposed on the overall system. Skilled artisans may implement the described functionality in varying ways for each particular application, but such implementation decisions should not be interpreted as causing a departure from the embodiments described herein.

Accordingly, it will be understood that the invention is not to be limited to the embodiments disclosed herein and extend to the subject matter of the claims herein.

The invention claimed is:

1. An ultrasound imaging system having a handheld device and a probe that generates ultrasound images, comprising:

a user interface (UI) control button disposed on the probe, a power control module configured to activate a low-power mode to reduce power consumed by at least one of the hand held device and the probe, and to generate a wakeup configuration signal representative of a command to reconfigure a function of the UI control button, a preset memory for storing a preset parameter for configuring the probe for a predetermined imaging procedure and wherein the power control module is configured to process the preset parameter to determine whether the preset parameter indicates that the predetermined imaging procedure is a sterile imaging procedure, and a reconfiguration module configured to receive the wake-up configuration signal and determine if the preset parameter indicates the sterile imaging procedure, and in response to receiving the wake-up configuration signal and an indication of the sterile imaging procedure, reconfigure an interface coupled to the UI control button to detect activation of the UI control button and, in response to activation of the UI control button, the interface deactivates the low-power mode to have the handheld device and the probe consume power sufficient to perform imaging procedures.

2. The ultrasound imaging system of claim 1, wherein the preset memory stores preset parameters for a plurality of predetermined imaging procedures and stores a timeout period for each of the respective predetermined imaging procedures.

3. The ultrasound imaging system of claim 1, wherein the preset memory stores an override parameter representative of an operator instruction for the reconfiguration module to override the preset parameters for a predetermined imaging procedure and implement the operator instruction for reconfiguring the UI control button.

4. The ultrasound imaging system of claim 1 wherein the reconfiguration module deactivates the low-power mode by sending a signal to the power control module to activate a power mode sufficient to perform imaging procedures.

5. The ultrasound imaging system of claim 1 wherein the probe is a hand-held ultrasound probe having a transducer for transmitting and receiving ultrasound signals and a housing connected to the transducer and shaped to allow a clinician to grip the probe with a hand and thereby position the transducer proximate a patient and wherein the UI control button is disposed on the housing at a location that can be reached by a hand holding the probe.

6. The ultrasound imaging system of claim 1, wherein the UI control button, when not in low-power mode, is configured to operate a different function of the probe to generate a reading of remaining battery power or perform an image capture procedure to capture ultrasound images.

7. The ultrasound imaging system of claim 1, further comprising a timer module configured to generate a timeout signal, wherein the power control module activates the low-power mode responsive to receiving the timeout signal from the timer module wherein the timeout signal represents expiration of a timeout period.

8. The ultrasound imaging system of claim 7 further comprising a data memory that stores a preset timeout parameter representative of a timeout period, and wherein the timer module counts down in response to the stored preset timeout period to generate the timeout signal.

9. The ultrasound imaging system of claim 7 further comprising an image comparator module to detect changes in a sequence of ultrasound images and to reset the timer module responsive to detecting changes in the sequence of ultrasound images.

10. A method for ultrasound imaging using a handheld device and a probe with a user interface (UI) control button disposed on the probe, comprising:

activating a low-power mode to reduce power consumed by at least one of the hand held device and the probe, generating a wake-up configuration signal representative of a command to reconfigure a function of the UI control button, storing, in a preset memory, a preset parameter for configuring the probe for a predetermined imaging procedure, processing the preset parameter to determine whether the preset parameter indicates that the predetermined imaging procedure is a sterile imaging procedure, in response to receiving, at a reconfiguration module, the wake-up configuration signal and an indication of the sterile imaging procedure, reconfiguring an interface coupled to the UI control button to detect activation of the UI control button, and in response to activation of the UI control button, the interface deactivating the low-power mode to have the handheld device and the probe consume power sufficient to perform imaging procedures.

11. The method for ultrasound imaging of claim 10, wherein storing preset parameters includes storing preset parameters for a plurality of predetermined imaging procedures and storing a timeout period for each of the respective predetermined imaging procedures.

12. The method for ultrasound imaging of claim 10, further comprising providing a memory for storing an override parameter representative of an operator instruction to override the wake-up configuration signal and thereby prevent reconfiguring the interface.

13. The method for ultrasound imaging of claim 10, further comprising providing the probe as a hand-held ultrasound probe having a transducer for transmitting and receiving ultrasound signals and a housing shaped to allow a clinician to grip the probe with a hand and disposing the UI control button on the probe at a location that can be reached by a hand holding the probe.

14. The method for ultrasound imaging of claim 10, wherein the UI control button, when not in low-power mode, is configured to operate a different function of the probe to generate a reading of remaining battery power or perform an image capture procedure to capture ultrasound images.

15. The method for ultrasound imaging of claim 10, further comprising providing a timer module configured to generate a timeout signal, and activating the low-power mode responsive to the timeout signal from the timer module wherein the timeout signal represents expiration of a timeout period.

16. The method for ultrasound imaging of claim 15, further comprising storing a preset timeout parameter representative of a timeout period, and wherein the timer module counts down from the stored preset timeout parameter to generate the timeout signal.

17. The method for ultrasound imaging of claim 15, further comprising detecting changes in a sequence of ultrasound images and resetting the timer module to the timeout period in response to detecting changes in the sequence of ultrasound images.

18. The method for ultrasound imaging of claim 17, wherein detecting changes in a sequence of images includes performing an edge detection and comparison process to determine whether similar edges of images the sequence of images are changing.

* * * * *